US012742161B2

(12) United States Patent
Zhang et al.

(10) Patent No.: US 12,742,161 B2
(45) Date of Patent: Sep. 22, 2026

(54) INACTIVE TELOMERASE, ADENOVIRUS ASSOCIATED VIRUS AND ARTIFICIAL MRNA HAVING SAME AND USE THEREOF

(71) Applicants: Zhejiang Juvensis Therapeutics Co., Ltd., Taizhou (CN); Nanjing Juvensis Therapeutics Co., Ltd., Nanjing (CN)

(72) Inventors: Jiahao Zhang, Nanjing (CN); Xue Zeng, Taizhou (CN)

(73) Assignees: Zhejiang Juvensis Therapeutics Co., Ltd., Taizhou (CN); Nanjing Juvensis Therapuetics Co., Ltd., Nanjing (CN)

( * ) Notice: Subject to any disclaimer, the term of this patent is extended or adjusted under 35 U.S.C. 154(b) by 644 days.

(21) Appl. No.: 18/027,838

(22) PCT Filed: Sep. 22, 2021

(86) PCT No.: PCT/CN2021/119552

§ 371 (c)(1),
(2) Date: Mar. 22, 2023

(87) PCT Pub. No.: WO2022/063108

PCT Pub. Date: Mar. 31, 2022

(65) Prior Publication Data

US 2023/0340431 A1 Oct. 26, 2023

(30) Foreign Application Priority Data

Sep. 22, 2020 (CN) ......................... 202010999930.8

(51) Int. Cl.

| | |
|---|---|
| ***C12N 9/12*** | (2006.01) |
| ***A61K 48/00*** | (2006.01) |
| ***A61P 9/00*** | (2006.01) |
| ***C12N 7/00*** | (2006.01) |
| *A61K 38/00* | (2006.01) |

(52) U.S. Cl.

CPC .......... *C12N 9/1276* (2013.01); *A61K 48/005* (2013.01); *A61P 9/00* (2018.01); *C12N 7/00* (2013.01); *C12Y 207/07049* (2013.01); *A61K 38/00* (2013.01); *C12N 2750/14122* (2013.01)

(58) Field of Classification Search

None

See application file for complete search history.

(56) References Cited

FOREIGN PATENT DOCUMENTS

| | | | |
|---|---|---|---|
| CN | 1432411 | A | 7/2003 |
| CN | 105164269 | A | 12/2015 |
| CN | 106061509 | A | 10/2016 |
| CN | 108473956 | A | 8/2018 |
| CN | 112063601 | A | 12/2020 |
| WO | 1998/014593 | A2 | 4/1998 |
| WO | 2012/001170 | A1 | 1/2012 |
| WO | 2014/130909 | A1 | 8/2014 |
| WO | 2016/020345 | A1 | 2/2016 |
| WO | 2016/020346 | A1 | 2/2016 |

OTHER PUBLICATIONS

Singh et al. (Curr. Protein Pept. Sci. 18:1-11, 2017).*
Zhang et al. (Structure 26:1474-1485, 2018).*
Sachsinger et al. (Cancer Res., vol. 61, pp. 5580-5586, Jul. 2001) .*
Ngo et al. in The Protein Folding Problem and Tertiary Structure Prediction, 1994, Merz et al. (ed.), Birkhauser, Boston, MA, pp. 433 and 492-495.*
Franceus et al., (J. Ind. Microbiol. Biotechnol. vol. 44, pp. 687-695, 2017).*
Jakob, Sascha et al., "Nuclear Protein Tyrosine Phosphatase Shp-2 Is One Important Negative Regulator of Nuclear Export of Telomerase Reverse Transcriptase," Journal of Biological Chemistry, vol. 283, No. 48, pp. 33155-33161, 2008.
Saretzki, G., Extra-telomeric Functions of Human Telomerase: Cancer, Mitochondria and Oxidative Stress, Current Pharmaceutical Design (2014) 20, pp. 1-18.
Ramunas, John et al., Transient delivery of modified mRNA encoding TERT rapidly extends telomeres in human cells, The FASEB Journal (May 2015) 29(5), pp. 1930-1939.
Bernardes De Jesus, Bruno et al., Telomerase gene therapy in adult and old mice delays aging and increases longevity without increasing cancer, EMBO Molecular Medicine (2012) 4, pp. 691-704.
Oh, Hidemasa et al., Telomerase reverse transcriptase promotes cardiac muscle cell proliferation, hypertrophy, and survival, PNAS (Aug. 28, 2001) vol. 98, No. 18, pp. 10308-10313.
Haendeler, Judith et al., Hydrogen Peroxide Triggers Nuclear Export of Telomerase Reverse Transcriptase via Src Kinase Family-Dependent Phosphorylation of Tyrosine 707, Molecular and Cellular Biology (Jul. 2003) vol. 23, No. 13, pp. 4598-4610.
Office Action dated Jan. 9, 2023 relating to Chinese Patent Application No. 202010999930.8, 3 pages.
Office Action dated Mar. 11, 2022 relating to Chinese Patent Application No. 202010999930.8, 5 pages.

* cited by examiner

*Primary Examiner* — Richard G Hutson
(74) *Attorney, Agent, or Firm* — Stinson LLP

(57) ABSTRACT

The present invention discloses an inactive telomerase, which is a double mutant telomerase having double mutation sites Y707F and D868A. The present invention also discloses an adenovirus-inactive telomerase and an artificial mRNA-inactive telomerase having double mutation sites, and use thereof in the treatment of diseases associated with non-dividing cell telomere shortening. The present invention is capable of inhibiting the activity of telomerase TERT in non-dividing cells to form an inactive telomerase CI-TERT and simultaneously preventing the telomerase from leaving the nucleus. By such configuration, the telomerase can be kept in the nucleus to protect the telomeric ends from shortening and prevent telomerase from causing telomere lengthening to the extent of cell carcinogenesis, thus reducing the risk of carcinogenesis and keeping the telomerase in the nucleus to protect the telomeric ends and inhibiting the deterioration of the disease caused by telomere shortening.

13 Claims, 4 Drawing Sheets

TelC cTnT DAPI

INACTIVE TELOMERASE, ADENOVIRUS ASSOCIATED VIRUS AND ARTIFICIAL MRNA HAVING SAME AND USE THEREOF

FIELD OF INVENTION

The present invention relates to the technical field of genetic engineering and cytology. Specifically, it relates to an inactive telomerase and use thereof.

BACKGROUND OF INVENTION

Telomere is a complex of multiple repeats of non-transcribed DNA (Deoxyribonucleic Acid) and proteins at the terminals of human eukaryotic chromosomes. Telomeres have been shown in studies to be associated with aging, cell division control, and disease. Telomerase, an enzyme responsible for telomere lengthening in cells, is a basic nuclear protein reverse transcriptase that adds telomeric DNA to the terminals of eukaryotic chromosomes to extend the telomeres lost in DNA replication, allowing the repaired telomeres to be lengthened so that telomeres are not lost in the cell division.

In recent decades, gene therapy has gradually transformed from scientist's dream to a reality. The vector for gene therapy has always been the key to the whole gene therapy. Currently, AAV (Adenovirus Associated Virus) is a widely investigated gene therapy vector due to its ability to integrate into human chromosomes through transfection. However, the cell-specific discrimination of AAV in humans can be limiting and the virus has a risk of inducing an cytokine storm. It has been shown in studies that telomere shortening is closely associated with a variety of diseases and aging, and that lengthening telomere can slow down diseases or have some therapeutic effects. Currently, the telomere lengthening is achieved in the laboratory by directly injecting adenovirus-telomerase AAV-TERT into the experimental models and over-expressing active telomerase. However, this non-specific design does not eliminate a possibility that cells with mutations may transform into cancer cells after receiving the active telomerase. Therefore, how to lock telomerase in the nucleus to protect telomeric ends, inhibit telomere shortening induced disease deterioration while reducing the risk of carcinogenesis is a direction that needs to be investigated by those skilled in the art.

SUMMARY OF INVENTION

To overcome the defects and deficiencies of the prior art, the present invention aims to provide an inactive telomerase, an adenovirus-inactive telomerase and an artificial mRNA-inactive telomerase having the same and use thereof.

In order to achieve the above objects, according to a first aspect of the present invention, there is provided an adenovirus-inactive telomerase, said adenovirus-inactive telomerase comprising a double mutant telomerase, having Y707F and D868A as the double mutations, respectively.

According to a second aspect of the present invention, there is provided an adenovirus-inactive telomerase, and said adenovirus-inactive telomerase comprising a double mutant telomerase, and the double mutation sites being Y707F and D868A, respectively.

According to a third aspect of the present invention, there is provided an artificial mRNA-inactive telomerase, comprising a double mutant telomerase having Y707F and D868A as the double mutation sites, respectively.

According to a fourth aspect of the present invention, there is provided use of the aforementioned adenovirus-inactive telomerase or the artificial mRNA-inactive telomerase in the treatment of diseases associated with telomere shortening in non-dividing cells.

Further, said non-dividing cells include a cardiomyocyte, a skeletal muscle cell and a nerve cell.

Further, said diseases associated with telomere shortening in non-dividing cells preferably include a disease associated with telomere shortening in cardiomyocyte.

Further, said diseases associated with telomere shortening in cardiomyocyte include dilated cardiomyopathy (DCM), hypertrophic cardiomyopathy (HCM), nuclear fibrillar protein disease and telomere shortening-related rare heart disease.

Further, said telomere shortening-related rare heart disease includes Duchenne muscular dystrophy DMD.

In according to the above technical solutions, the present invention provides a double mutation inactive telomerase (CI-TERT, Catalytically Inactive TERT) having Y707F and D868A as the mutation sites, wherein the site mutation of Y707F allows the telomerase to remain in the nucleus, and the restriction of leaving would allow telomerase to bite at telomeric ends for a long term to form a protective structure. The site mutation of D868A allows the telomerase to lose activity, and such inactivation of telomerase would prevent uncontrolled telomere lengthening and the possibility of cancer induction. To achieve the function of the double mutation inactive telomerase, the applicants discovered that both an adenovirus and an artificial mRNA can be used as vectors for double mutation inactive telomerase, and by injecting an adenovirus-inactive telomerase and/or an artificial mRNA-inactive telomerase into the target cells, a double mutation inactive telomerase can be produced in the target cells. That is, the technical solution of the present invention can produce a double mutation inactive telomerase in the target cells, and through an over-expression of the inactive telomerase CI-TERT, the double mutation inactive telomerase can perform the corresponding function through the mutual cooperation of the double mutation sites, which not only reduces the risk of cell carcinogenesis, but also keeps the telomerase in the nucleus to protect the telomeric ends and inhibit the deterioration of the disease caused by telomere shortening.

In comparison with the prior art, the present invention achieves the following beneficial effect:

1. preventing the telomere from shortening, preventing and treating a plurality of diseases associated with a telomere shortening, especially a telomere shortening in a non-dividing cell, and aging.
2. being capable of preserving telomere lengths in a plurality of diseases associated with a telomere shortening, especially a telomere shortening in a non-dividing cell, and in aging cells, with some therapeutic effect of slowing down the diseases.
3. inhibiting a cell death caused by a telomere shortening.
4. protecting telomeric ends, and preventing a risk of a cellular carcinogenesis caused by a telomere overgrowth.

DESCRIPTION OF DRAWINGS

The drawings accompanying the specification and forming part of the present application are used to provide a further understanding of the present invention. The schematic embodiments of the present invention and the descriptions thereof are used to explain the present invention and do not constitute an undue limitation of the present invention. In the accompanying drawings.

DETAILED DESCRIPTION OF INVENTION

The present invention is described in further detail end below by means of specific embodiments and examples and in conjunction with the accompanying drawings. It is to be noted that the embodiments and the features in the embodiments of the present application can be combined with each other, without contradicting each other. The present invention will be described in details hereinafter by reference to the accompanying drawings and in conjunction with the embodiments.

Figure 1:
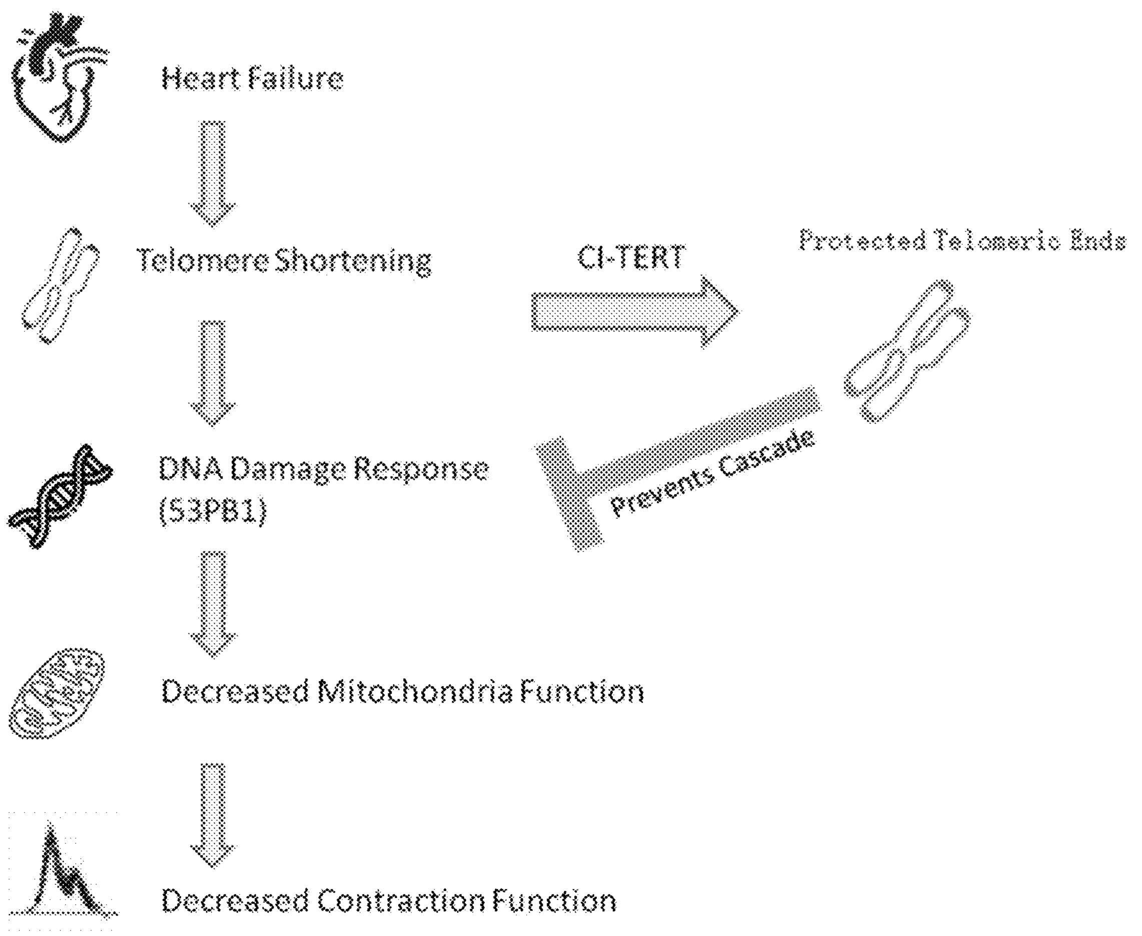
FIG. 1 illustrates a flow chart of the working principle of the present invention.

According to a typical embodiment of the present invention, there is provided an inactive telomerase, which is a double mutant telomerase having Y707F and D868A as the double mutations, respectively. A flow chart of the working principle of the present invention is illustrated in FIG. 1.

In according to the above technical solutions, the site mutation of Y707F allows the telomerase to remain in the nucleus, and prevents the telomerase from leaving, which allows telomerase to bite at the telomeric ends for a long term to form a protective structure; and the site mutation of D868A causes the telomerase to lose activity, and such inactivation of telomerase would prevent uncontrolled telomere lengthening and the possibility of cancer induction. The present invention provides a double mutation inactive telomerase CI-TERT having Y707F and D868A as mutation sites, which not only inhibits the activity of telomerase TERT to obtain an inactive telomerase CI-TERT, but also prevents the telomerase from leaving the nucleus. Through the mutual cooperation of the double mutation sites of Y707F and D868A, telomerase is kept in the nucleus to protect the telomeric ends, which allows the telomerase to bite at the telomeric ends for a long time to form a protective structure; and uncontrolled telomere lengthening and possible cell carcinogenesis caused by telomerase activity is prevented. Therefore, the double mutation inactive telomerase CI-TERT provided by the present invention is able to keep telomerase in the nucleus to protect the telomeric ends, and inhibits disease deterioration due to telomere shortening, while reducing the risk of carcinogenesis.

According to a typical embodiment of the present invention, there is provided an adenovirus-inactive telomerase, the adenovirus-inactive telomerase AAV-CI-TERT comprises a double mutant telomerase having Y707F and D868A as double mutation sites, respectively. The adenovirus-inactive telomerase AAV-CI-TERT of this embodiment is prepared by the following steps of, S1, culturing plasmid of the above-mentioned double mutation inactive telomerase CI-TERT having Y707F and D868A at mutation sites, respectively, using bacteria.

S2, transfecting said double mutation inactive telomerase CI-TERT plasmid into adenovirus-293T or AAV-293T cells by lipid transfecting amine, i.e. Lipofectamin, and culturing.

S3, after 7 days of culturing, extracting the adenovirus or AAV virus containing the double mutation inactive telomerase CI-TERT plasmid by centrifugation.

Accordingly, it is obtained the double mutation adenovirus-inactive telomerase CI-TERT or AAV virus-inactive telomerase CI-TERT having Y707F and D868A as mutation sites, respectively.

The extracted adenovirus comprising the double mutation inactive telomerase CI-TERT plasmid or AAV virus adenovirus comprising the double mutation inactive telomerase CI-TERT plasmid is added to a culture medium (cell culture) for a culture of 24-48 hours and then the culture medium is changed, or is injected into the target cells to observe whether the target cells produce adenovirus-inactive telomerase or AAV-CI-TERT on its own.

In each of the above steps, a successful transformation of the inactive telomerase CI-TERT plasmid with double mutations can be demonstrated by a genetic testing. The desired effect can also be demonstrated by an immunofluorescence staining performed on an animal models or biological samples after injection or infusion.

Specifically, the above immunofluorescence staining comprises the steps of:

1. Sample staining: the sample is indicated with a cut-off pen by drawing around the sample, Telomeric Peptide Nucleic Acid PNA Antibody of 10 micrograms per milliliter (ug/mL) is added to stain the TelC telomeric repeat sequence, and the slide is placed in a stained box to prevent light exposure. The samples are covered with a coverslip and put in an oven at 84 degrees Celsius for 7 minutes. The coverslips are removed, the samples are washed twice with PNA washing solution for 15 minutes each, followed by two washes with PBST for 5 minutes each. After washing, the slides are blocked at RT stained using a blocking solution, prepared using 10% calf serum plus phosphate buffered salt solution, for 1 hour, and then stained at RT using a thousand-fold dilution of anti-cardiac tubercle (cTnT) primary antibody for 2 hours. The samples are washed with the blocking solution three times for 5 minutes each, and then stained using with an anti-mouse 488alexa488 secondary antibody diluted 1:1000 for 1 hour. After washing twice with each of Peptide Nucleic Acid PNA washing solution and PBST for 15 minutes each, a nuclear stain DAPI is added at a total concentration of 1 μg/mL in molecule-free pure water for a 5 minute-staining. The samples are washed 3 times with phosphate buffered salt solution for 5 minutes each, and sealed with slide sealing agent and stored at four degrees Celsius until photographed on the machine.

2. Telomere length measurement: Telometer (a software measuring telomeric end length), an ImageJ plug-in developed by Prof Alan Meeker's lab at Hawkins University, is used to measure telomere length by the fluorescence intensity of DAPI in the nucleus in contrast with TelC in selected nucleus in photographs of stained samples.

By the above technical solution, an adenovirus with inactive telomerase CI-TERT plasmid or AAV virus with inactive telomerase CI-TERT plasmid is injected into the target cells to produce a double mutation inactive telomerase CI-TERT in the target cells, and the double mutation sites interacted, in which, mutation site Y707F makes telomerase remain in the nucleus of the target cells, restricts telomerase from leaving and makes telomerase bite at the terminal of the telomere for a long time to form a protective structure; and Mutation site D868A makes telomerase inactive, and inactivation of telomerase will prevent uncontrolled telomere lengthening and the malignant tumor generation. The technical solution of the present invention uses AAV as a vector to successfully inject the double mutation inactive telomerase into the target cells to produce the double mutation inactive telomerase CI-TERT in the target cells, which keeps the telomerase in the nucleus to protect the telomeric ends and inhibit the deterioration of disease caused by telomere shortening while reducing the risk of carcinogenesis.

According to a typical embodiment of the present invention, there is provided an artificial mRNA-inactive telomerase comprising a double mutant telomerase, which having Y707F and D868A as the double mutation sites, respectively. An DNA nucleic acid sequence of the artificial mRNA-inactive telomerase may be produced as below.

The artificial mRNA, also known as mmRNA, is an artificial messenger RNA, and the artificial mRNA-inactive telomerase or mmRNA-CI-TERT used in this example is an artificial mRNA-inactive telomerase or mmRNA-CI-TERT having the double mutation of Y707F (retained in the nucleus) and D868A (inactive). The double mutation artificial mRNA-inactive telomerase, or mmRNA-CI-TERT having Y707F and D868A as mutation sites, respectively, is injected into the target cells to observe whether the target cells produce the artificial mRNA-inactive telomerase, or mmRNA-CI-TERT, on its own.

In each of the above steps, a successful transformation of the inactive telomerase CI-TERT plasmid having double mutations can be demonstrated by a genetic testing. The desired effect can also be demonstrated by immunofluorescence staining on animal models or biological samples after injection or infusion.

Specifically, the above immunofluorescence staining comprises the steps of,

1. Sample staining: the sample is indicated with a cut-off pen by drawing around the sample, Telomeric Peptide Nucleic Acid PNA Antibody of 10 micrograms per milliliter (ug/mL) is added to stain the TelC telomeric repeat sequence, and the slide is placed in a stained box to prevent light exposure. The samples are covered with a coverslip and put in an oven at 84 degrees Celsius for 7 minutes. The coverslips are removed, the samples are washed twice with PNA washing solution for 15 minutes each, followed by two washes with PB ST for 5 minutes each. After washing, the slides are blocked at RT stained using a blocking solution, prepared from 10% calf serum plus phosphate buffered salt solution, for 1 hour, and then stained at RT using a thousand-fold dilution of anti-cardiac tubercle (cTnT) primary antibody for 2 hours. The samples are washed with the blocking solution three times for 5 minutes each, and then stained using with an anti-mouse 488alexa488 secondary antibody diluted 1:1000 for 1 hour. After washing twice with each of Peptide Nucleic Acid PNA washing solution and PBST for 15 minutes each, a nuclear stain DAPI is added at a total concentration of 11 μg/mL in molecule-free pure water for a 5 minute-staining. The samples are washed 3 times with phosphate buffered salt solution for 5 minutes each, and sealed with slide sealing agent and stored at four degrees Celsius until photographed on the machine.

2. Telomere length measurement: telometer (a software measuring telomeric end length), an ImageJ plug-in developed by Prof. Alan Meeker's lab at Hawkins University, is used to measure telomere length by the fluorescence intensity of DAPI in the nucleus in contrast with TelC in selected nucleus in photographs of stained samples.

By the above technical solution, an artificial mRNA and/or mmRNA comprising double mutation inactive telomerase CI-TERT plasmid having Y707F and D868A as mutation sites, respectively is injected into the target cells to produce a double mutation inactive telomerase CI-TERT in the target cells, and the double mutation sites interact, in which, mutation site Y707F makes telomerase remain in the nucleus of the target cells, restricts telomerase from leaving and so that telomeres do not shorten; and Mutation site D868A mutation makes telomerase inactive, and inactivation of telomerase will prevent uncontrolled telomere extending and the possibility of inducing cancer. The technical solution of the present invention uses artificial mRNA or mmRNA as a vector to successfully inject the double mutation inactive telomerase into the target cells to produce the double mutation inactive telomerase CI-TERT in the target cells, which keeps the telomerase in the nucleus to protect the telomeric ends and inhibit the deterioration of disease caused by telomere shortening while reducing the risk of carcinogenesis.

According to a typical embodiment of the present invention, there is provided use of the adenovirus-inactive telomerase in the above embodiment or the artificial mRNA-inactive telomerase in the above embodiment in the treatment of diseases associated with telomere shortening in non-dividing cells.

Notably, the telomere shortening in non-dividing cells causes aging, cell division control, and other diseases. By the technical solution of the present invention, a double mutation inactive telomerase is produced in the target cells by the adenovirus-inactive telomerase AAV-CI-TERT or artificial mRNA-inactive telomerase mmRNA-CI-TERT. The site mutation of Y707F allows the telomerase to remain in the nucleus of target cells, and prevents the telomerase from leaving, which allows the telomerase to bite at the telomeric ends for a long term to form a protective structure. The site mutation of D868A allows the telomerase to lose activity, and such inactivation of telomerase would prevent uncontrolled telomere extending and the possibility of inducing cancer. Therefore, the technical solution of the present invention can successfully generate double mutation inactive telomerase CI-TERT in the receptor, effectively control the expression of telomerase and the type of target cells, and keep telomerase in the nucleus and protect the telomeric ends through overexpression of the telomerase with activity with reduced risk of cancer, which prevents telomere from shortening, inhibits cell death and disease deterioration caused by telomere shortening in non-dividing cells. Thus, it is possible to prevent and treat a plurality of diseases associated with a telomere shortening and aging, enabling the telomere in the plurality of diseases associated with a telomere shortening and aging cell to lengthen, and achieving therapeutic effects of slowing down the diseases.

Preferably, the non-dividing cells include a cardiomyocyte, a skeletal muscle cell, and a nerve cell. Non-dividing cells include, but not limited to, cardiomyocytes, skeletal muscle cells, and nerve cells, among others. The abnormalities and diseases may occur in cardiac myocytes, skeletal muscle cells, and nerve cells ect. due to the occurrence of telomere shortening or step-wised shortening. Double mutant telomerase can effectively control the expression of telomerase and the type of target cells in non-dividing cells to achieve the appropriate function.

Preferably, said diseases associated with telomere shortening in non-dividing cells preferably comprises a disease associated with telomere shortening in cardiomyocyte.

Preferably, said diseases associated with telomere shortening in cardiomyocyte include dilated cardiomyopathy (DCM), hypertrophic cardiomyopathy (HCM), nuclear fibrillar protein disease and telomere shortening-related rare heart disease.

More preferably, said telomere shortening-related rare heart disease includes Duchenne muscular dystrophy DMD.

Studies have shown that the telomere shortening in cardiomyocyte is the cause of rare heart diseases such as Duchenne muscular dystrophy DMD disease and death. Other diseases associated with telomere shortening in cardiomyocyte include Laminopathy, most of the dilated cardiomyopathies in Titinopathy, and Hypertrophic Cardiomyopathy (HCM). The applicant found that the disease associated with telomere shortening in cardiomyocytes manifests as telomere phased-shortening. The diseases caused by telomere shortening are not limited to hereditary cardiomyopathies, and it have been found that telomere shortening is associated with a range of diseases. With the technical solution of the present invention, using adenovirus or artificial mRNA as a vector, a double mutation inactive telomerase having Y707F and D868A as mutation sites, respectively, is injected into receptor cardiomyocytes, and a double mutation inactive telomerase with Y707F and D868A is successfully produced in the receptor cardiomyocytes. The mutation site Y707F mutation makes telomerase remain in the nucleus of the target cells and the restriction of leaving would keep telomeres from shortening. The site mutation of D868A causes the telomerase to lose activity, and such inactivation of telomerase would prevent uncontrolled telomere lengthening. For the abnormal telomere phased-shortening in cardiomyocytes, the double mutation inactive telomerase of the present invention not only ameliorates the continuous deterioration of the disease caused by the telomerase phased-shortening, but also prevents the occurrence of telomere shortening by the intervention at an early enough time. The applicant has also found, after extensive experiments, that telomere shortening due to heart failure causes nucleic acid damage, leading to a decrease in mitochondrial function and number, which in turn affects myocardial contractile function. Protection of telomeric ends by the inactive telomerase CI-TERT prevent disease deterioration and prevents nucleic acid damage, decrease in mitochondrial function and number, and decrease in myocardial function.

The beneficial effects of the present invention will be further illustrated below in conjunction with the Examples.

EXAMPLES

According to a typical example of the present invention, an adenovirus-inactive telomerase AAV-CI-TERT was used to treat a heart disease.

Figure 2:
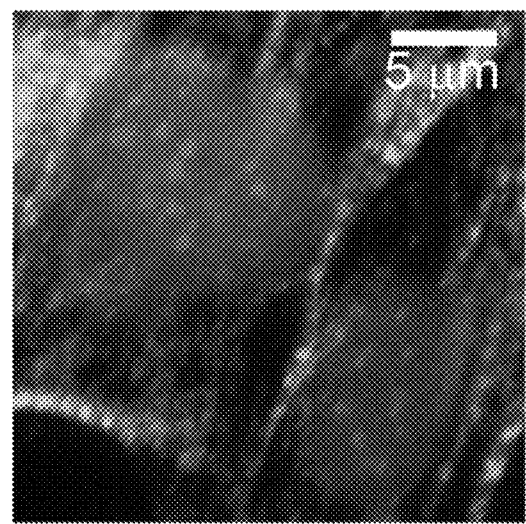
FIG. 2 illustrates a schematic diagram of measuring telomeres length by quantitative fluorescence in situ hybridization (QFISH) localization of telomeres (telomere repeat sequence stained using TelC) by in healthy cardiomyocytes (myocardial sarcomere stained using cardiac troponin T, cTnT).
Figure 3:
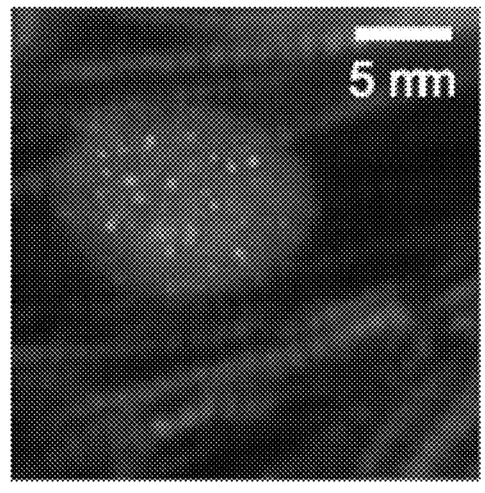
FIG. 3 illustrates a schematic diagram of measuring telomeres length by QFISH localization of telomeres (telomere repeat sequence stained using TelC) by in diseased cardiomyocytes (myocardial sarcomere stained using cTnT).

The measurement of telomeric ends length in cardiac sections from patients with cardiomyopathy by immunofluorescence staining revealed an abnormal telomere shortening in patients with cardiomyopathy, which gradually causes cell death and leads to deterioration and heart failure. Notably, telomere shortening was not detected in other biological samples from the patients. This phenomenon was also observed experimentally in cardiomyocytes differentiated from human-derived stem cells, and the telomere length in the nucleus of cardiomyocytes differentiated from human-derived stem cells could be located and measured by immunofluorescence staining, as shown in FIG. 2 and FIG. 3, demonstrating that cardiomyocytes differentiated from human-derived stem cells can be used as an experimental model for abnormal telomere shortening in heart disease. At the level of human-derived stem cells, there is no difference in telomere length between healthy and diseased cells. Compared to cardiomyocytes differentiated from healthy human-derived stem cells, cardiomyocytes differentiated from diseased human-derived stem cells exhibited telomere shortening. This indicates that the abnormal telomere shortening is caused by cardiomyocytes in a non-dividing state, whereas in normal conditions telomere shortening is caused during cell division and cells with short telomeres will be removed during division. Through repeated experiments, the applicant found that the abnormal telomere shortening is caused by the reactive oxygen species (ROS) during disease development, which trigger the protective mitochondrial function of telomerase, causing the telomerase to leave the nucleus and leaving the telomeric ends unprotected. The applicant further found that this abnormal telomere shortening is not an acute shortening, but a gradual shortening in a stepwise manner. This suggests that intervention or treatment at an early stage of the disease can effectively inhibit or prevent telomere shortening.

Table 1 shows the telomere length measurements of the patient's myocardial samples. Table 1 demonstrates that abnormal telomere shortening in non-dividing cells (cardiomyocytes) in patients with cardiomyopathy.

| Telomere measurement of patient myocardial section samples | Number of measured nuclei | Average | Standard Error |
|---|---|---|---|
| a. Healthy samples | 1110 | 12.33 kB | 0.33 |
| b. Disease samples | 1688 | 8.3 kB | 0.51 |
| a. vs b. | | $p < 0.001$ | |

Table 2 shows telomere length measurements of smooth muscle sections of patients, demonstrating that abnormal telomere shortening in patients with cardiomyopathy is present only in cardiomyocytes.

| Telomere measurement in patient smooth muscle cells | Number of samples | Average | Standard Error |
|---|---|---|---|
| a. Health samples | 846 | 4.25 | 0.19 |
| b. disease samples | 1078 | 4.70 | 0.65 |
| a. vs b. | | P = statistically insignificant | |

Table 3 shows the telomere length measurements of cardiomyocytes differentiated from human induced pluripotent stem cells (iPSC). It demonstrates that abnormal telomere shortening occurs in non-dividing diseased cardiomyocytes.

| Telomere measurement of patient induced pluripotent stem cells and cardiomyocytes differentiated from induced pluripotent stem cells | Number of samples | Average | Standard Error |
|---|---|---|---|
| a. healthy human induced pluripotent stem cells | 396 | 29.67 kB | 0.40 |
| b. disease human induced pluripotent stem cells | 862 | 29.58 kB | 0.27 |
| c. cardiomyocytes differentiated from healthy human induced pluripotent stem cells | 486 | 29.20 kB | 0.40 |
| d. cardiomyocytes differentiated from disease human induced pluripotent stem cells | 1760 | 13.23 kB | 0.12 |
| a. vs b. | | P = statistically insignificant | |
| a. vs c. | | | |
| a. vs d. | | P < 0.01 | |
| b. vs d. | | | |

Table 4 shows the telomere length tracing experiment, which demonstrates that this abnormal telomere shortening is not an acute shortening but a gradual stepwise shortening.

| Measurement of telomere length in cardiomyocytes differentiated from human induced pluripotent stem cells | | | | | |
|---|---|---|---|---|---|
| Period (days) | 20 | 22 | 24 | 26 | 30 |
| Cardiomyocytes(CM) differentiated from healthy human induced pluripotent stem cells | 33.25 kB | 33.22 kB | 32.63 kB | 33.72 kB | 28.60 kB |
| Cardiomyocytes differentiated from disease human induced pluripotent stem cells | 27.77 kB | 24.78 kB | 17.53 kB | 13.14 kB | 14.23 kB |

Figure 4:
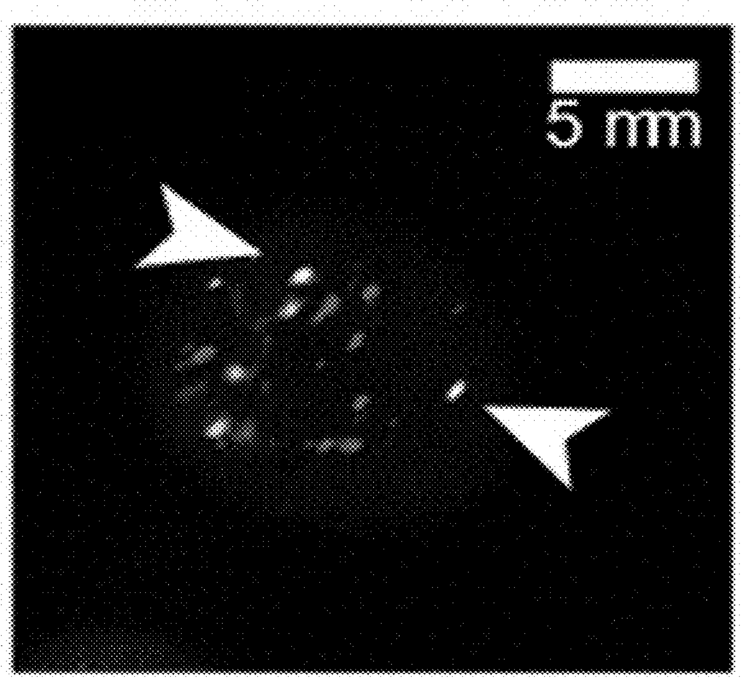
FIG. 4 illustrates a co-localized immunofluorescence staining, in diseased cardiomyocytes (myocardial sarcomere stained using cTnT), of telomeric ends (telomere repeat sequence stained using TelC) and damaged nucleic acids (nucleic acid damage signal stained using 53BP1).

By further comparing cardiomyocytes differentiated from healthy human-derived stem cells and cardiomyocytes differentiated from diseased patient's human-derived stem cells, it was found that diseased cells exhibit a higher nucleic acid damage signal 53BP1 at intranuclear telomeric tail end, as shown in FIG. 4, with a significantly lowered number of mitochondria and reduced cellular contractile function, i.e., reduced contractility.

Table 5 shows the measured nucleic acid damage signal in cardiac myocytes, demonstrating that there is more nucleic acid damage signal in cardiac myocytes in the disease.

| Detection of nucleic acid damage signal in cardiomyocytes | Proportion of positive reactions for 53BP1 (nucleic acid damage signal) |
|---|---|
| a. cardiomyocytes differentiated from healthy human induced pluripotent stem cells | 12.08 |
| b. cardiomyocytes differentiated from disease human induced pluripotent stem cells | 47.75 |
| a. vs b. | P < 0.0001 |

Table 6 shows the measurement of mitochondrial copy number in cardiomyocytes, demonstrating a significant decrease in the measurement of mitochondrial copy number in diseased cells.

| Measurement of mitochondrial copy number | Number of experiments | Average mitochondrial copy number |
|---|---|---|
| a. cardiomyocytes differentiated from healthy human induced pluripotent stem cells | 6 | 14345 |
| b. cardiomyocytes differentiated from disease human induced pluripotent stem cells | 6 | 5626 |
| a. vs b. | | P < 0.0005 |

Table 7 shows the measurement of contractility of cardiac myocytes, demonstrating that the function of diseased cell is affected and reduced. The results are shown in nano-newton, abbreviated as nN.

| Contractility measurement of cardiomyocytes differentiated from human induced pluripotent stem cells | Number of samples | Average (nN) | Standard Error |
|---|---|---|---|
| a. cardiomyocytes differentiated from healthy human induced pluripotent stem cells | 437 | 83.7 | 14.0 |
| b. cardiomyocytes differentiated from disease human induced pluripotent stem cells | 356 | 37.28 | 8.34 |
| a. vs b. | | P < 0.01 | |

Figure 5:
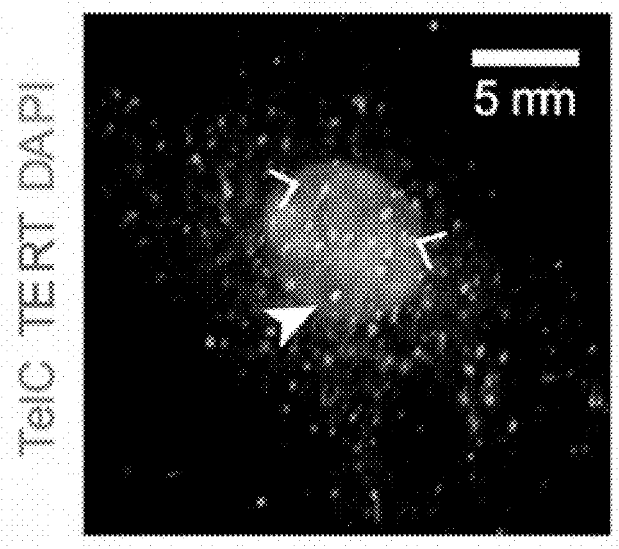
FIG. 5 illustrates a co-localized immunofluorescence staining in diseased cardiomyocytes of telomeric ends (telomeric repeat sequence stained using TelC) and telomerase (telomerase TERT).
Figure 6:
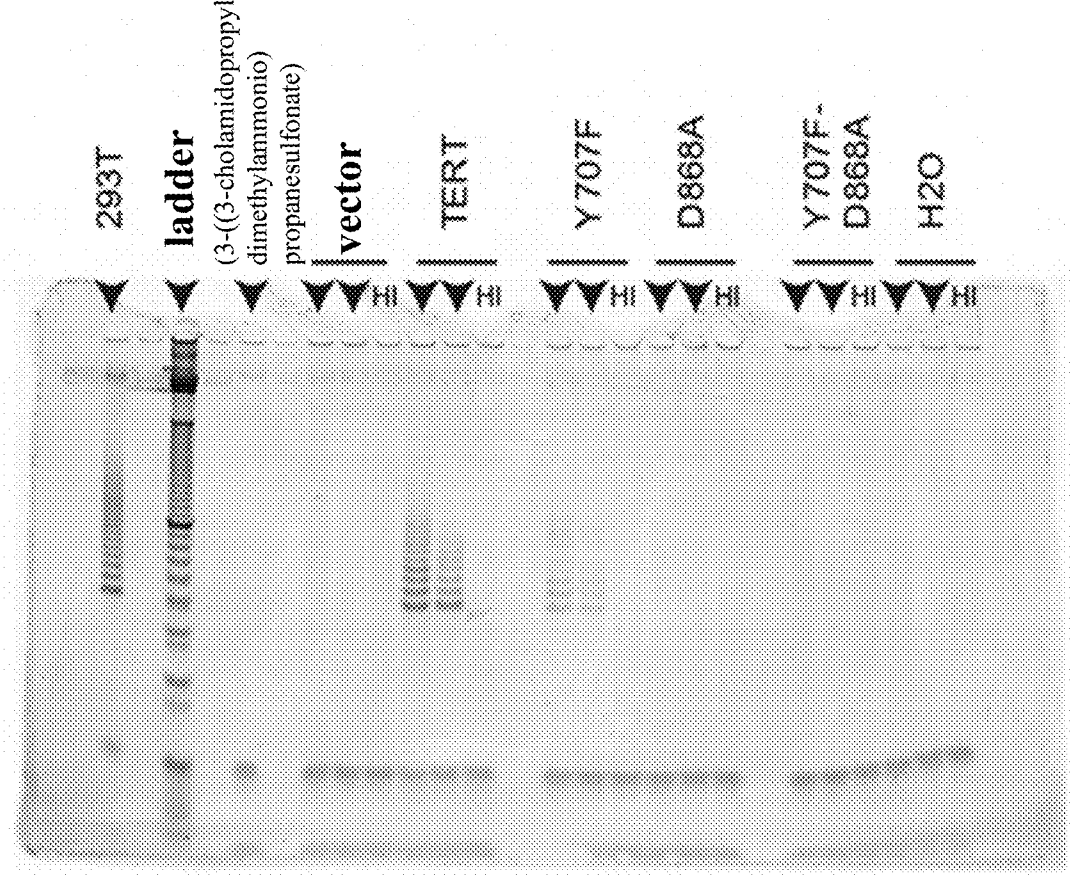
FIG. 6 is a drawing illustrating the telomerase activity assay (telomeric repeat amplification protocol, TRAP Assay).
Figure 7:
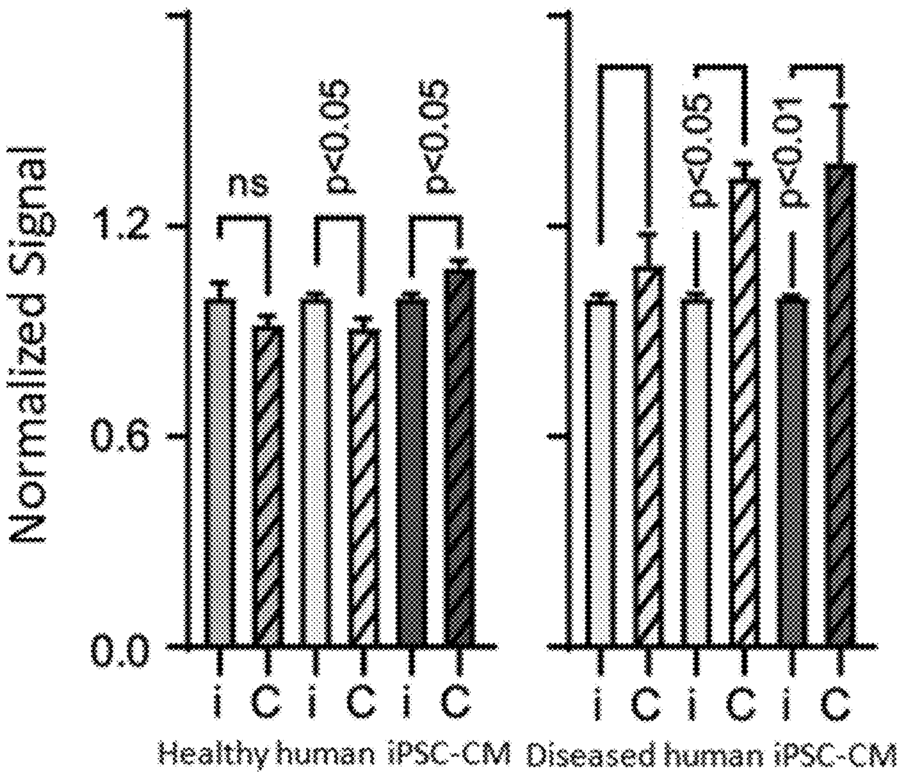
FIG. 7 is a drawing illustrating the assay of the co-localization of nucleic acid and protein (Chromatin Immunoprecipitation—quantitative PCR, ChIP-qPCR) experiment.

In order to inhibit telomere shortening and avoid excessive lengthening of telomeric ends, human telomerase sequences having two site mutations, called inactive telomerase or CI-TERT, were prepared in Examples of the present invention. The two mutation sites of the inactive telomerase or CI-TERT comprises Y707F, which keeps telomerase in the nucleus, and D868A, which renders telomerase inactive. The inactive telomerase was injected into the receptor via adenovirus (AAV) or artificial mRNA (mmRNA), that is, the adenovirus-inactive telomerase or artificial mRNA-inactive telomerase was injected into the receptor. As shown in FIG. 5, the receptor efficiently expressed this inactive telomerase and was specific for the telomeric ends in the nucleus. Notably, the receptor can be a cardiomyocyte model differentiated from human-derived stem cells and mouse model, or any other dividing cell. As shown in FIGS. 6 and 7, the inactive telomerase having double mutation in the technical solution of the present invention is inactive and specific for the exact telomeric tail end of the deprotected telomere, as demonstrated by the telomerase activity assay (TRAP Assay) (FIG. 6) as well as chromatin immunoprecipitation (ChIP) qPCR (ChIP-qPCR) (FIG. 7).

Table 8 shows qPCR measurements of CI-TERT expression, demonstrating that the receptor can over-express CI-TERT.

qPCR measurement of inactive telomerase CI-TERT expression

| Enrichment fold (normalized to blank media) | Blank media | Y707F-D868A |
|---|---|---|
| cardiomyocytes differentiated from disease human induced pluripotent stem cells | 1.0 | 3.57 |

Figure 8:
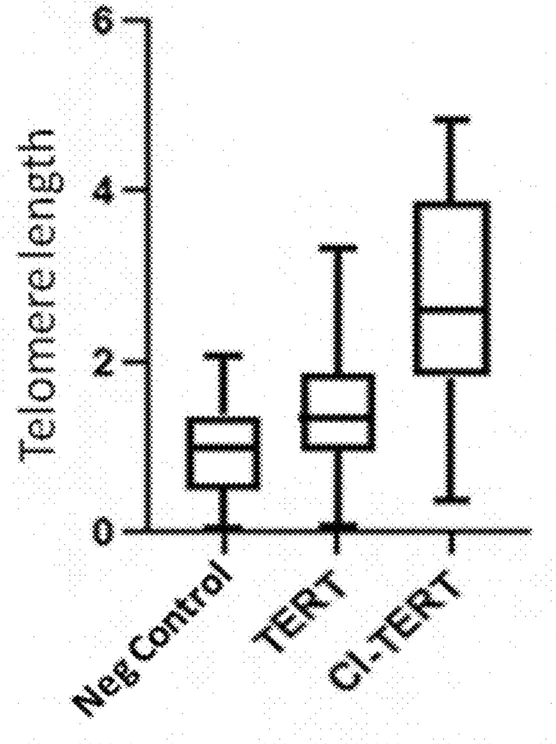
FIG. 8 illustrates a schematic diagram comparing the telomere length in a case of using an artificial mRNA-telomerase (mRNA-TERT) and in a case of using an artificial mRNA-inactive telomerase (mRNA-CI-TERT) in human-derived cardiomyocytes.

As shown in FIG. 8, it was further demonstrated that adenovirus-inactive telomerase or artificial-mRNA telomerase in Examples of the present invention can effectively protect telomeric ends from shortening, and inhibit a series of cellular responses such as, but not limited to, a nucleic acid damage, a decreased mitochondrial copy number, and a decreased contractility, caused by abnormal telomere shortening.

Table 9 shows the telomeric ends lengths measured after the injection of inactive telomerase CI-TERT, demonstrating that inactive telomerase CI-TERT effectively protects instead of lengthen telomeric ends.

Measurement of protection against telomeric end length by inactive telomerase CI-TERT

| | Number of samples | Average | Standard Error |
|---|---|---|---|
| a. cardiomyocytes differentiated from healthy human induced pluripotent stem cells | 486 | 29.20 kB | 0.40 |
| b. cardiomyocytes differentiated from disease human induced pluripotent stem cells | 956 | 11.69 kB | 0.13 |
| c. cardiomyocytes differentiated from disease human induced pluripotent stem cells + blank media | 433 | 12.03 kB | n/a |
| d. cardiomyocytes differentiated from disease human induced pluripotent stem cells + Y707F-D868A | 389 | 18.63 kB | 0.10 |
| b. v.s d. | | P < 0.001 | |

Table 10 shows the nucleic acid damage signal measured under the over-expression of CI-TERT, demonstrating that over-expression of CI-TERT is capable of reducing nucleic acid damage signal in cells.

| Detection of nucleic acid damage signal (53BP1) after the protection of inactive telomerase CI-TERT | Number of experi-ments | Average | Standard Error |
|---|---|---|---|
| a. cardiomyocytes differentiated from healthy human induced pluripotent stem cells | 6 | 12.08 | 2.04 |
| b. cardiomyocytes differentiated from disease human induced pluripotent stem cells | 6 | 47.75 | 3.05 |
| c. cardiomyocytes differentiated from disease human induced pluripotent stem cells + blank media | 3 | 57.28 | 1.49 |
| d. cardiomyocytes differentiated from disease human induced pluripotent stem cells + Y707F-D868A | 3 | 26.96 | 1.41 |
| b. vs d. | | p > 0.01 | |

Table 11 shows the number of mitochondria measured under over-expression of CI-TERT, demonstrating that the over-expression of CI-TERT is capable of effectively reducing mitochondrial death.

| Mitochondrial copy number rising after being protected by CI-TERT | Number of experiments | Mitochondrial copy number |
|---|---|---|
| cardiomyocytes differentiated from healthy human induced pluripotent stem cells | 6 | 14345 |
| cardiomyocytes differentiated from disease human induced pluripotent stem cells | 4 | 5626 |
| cardiomyocytes differentiated from disease human induced pluripotent stem cells + Y707F-D868A | 4 | 11073 |

Table 12 shows the cardiomyocyte contractility measured after the over-expression of CI-TERT, demonstrating that the over-expression of CI-TERT is capable of effectively protecting cardiomyocyte function.

| Restoration of cardiomyocyte contractility after protection by CI-TERT | Number of samples | Average (nN) | Standard Error |
|---|---|---|---|
| a. cardiomyocytes differentiated from healthy human induced pluripotent stem cells | 437 | 83.7 | 14.0 |
| b. cardiomyocytes differentiated from disease human induced pluripotent stem cells | 356 | 37.28 | 8.34 |
| c. cardiomyocytes differentiated from disease human induced pluripotent stem cells + blank media | 119 | 46.60 | 0.087079 |
| d. cardiomyocytes differentiated from disease human induced pluripotent stem cells + Y707F-D868A | 72 | 78.60 | 0.125189 |
| b. vs d. | | p = 0.017 | |

The experiments of the above Examples showed that the adenovirus-inactive telomerase in the technical solution provided by the present invention, by protecting telomeric ends, is effective in avoiding abnormal telomere shortening and damage to nucleic acids caused by the shortening, protecting mitochondrial function and thus cellular function, avoiding cell death as well as heart failure caused by disease deterioration.

In the case of cardiomyopathy, an abnormal telomeric ends shortening occurs in non-dividing cells, such as cardiomyocytes. The stepwise telomere shortening not only corresponds experimentally to the deterioration process of the disease observed clinically, but also indicates that an intervention at a sufficiently early enough stage prevents the deterioration of the disease, i.e., prevents the telomere persistent-shortening. It has been demonstrated by the experiments that the abnormal telomere shortening phenomenon can be simulated in cardiomyocytes differentiated from human-derived stem cells and that the inactive telomerase CI-TERT (Catalytically Inactive TERT) can effectively alleviate a series of indicators of this phenomenon. After extensive experiments, the applicant found that telomere shortening caused by heart failure causes nucleic acid damage, which leads to a decrease in mitochondrial function and number and thus affects the contractile function of the cardiac muscle. The protection of telomeric ends by inactive telomerase CI-TERT prevents the deterioration of the disease and prevents nucleic acid damage, decreased mitochondrial function and number, and decreased myocardial function.

The above-described Examples of the present invention provide the use of the above-described adenovirus-inactive telomerase in the treatment of diseases associated with telomere shortening in non-dividing cells. Therapeutic means of injecting adenovirus-inactive telomerase is able to control the expression of telomerase, and the type of target cells, with an effective vector to prevent diseases or symptoms caused by telomeric ends deprotection and shortening in such a non-dividing cell system as cardiomyocyte. The diseases associated with telomere shortening in cardiomyocytes include, but are not limited to, dilated cardiomyopathy DCM, hypertrophic cardiomyopathy HCM, nuclear fibrillar protein disease, and telomere shortening-related rare diseases such as Duchenne muscular dystrophy DMD. The diseased samples selected for the present Example include a plurality of diseases associated with telomere shortening in cardiomyocytes, such as, but are not limited to, dilated cardiomyopathy DCM, hypertrophic cardiomyopathy HCM, nuclear fibrillar protein disease HCM, nuclear fibrillar protein disease, and telomere shortening-related rare heart diseases such as Duchenne muscular dystrophy DMD.

Of course, the injection use of artificial mRNA-inactive telomerase mmRNA-CI-TERT instead of adenovirus-inactive telomerase is able to produce the same experimental effect. Both artificial mRNA and adenovirus as vectors for the double mutation inactive telomerase of the present invention, when injected into the receptor, can produce the double mutation inactive telomerase in the receptor, thus serving to maintain telomeres in the nucleus and protect telomere terminals from dislocation, treat and prevent diseases and cell death caused by telomere shortening.

In summary, the technical solution of the present invention inhibits the deterioration of diseases caused by telomere shortening by keeping telomerase in the nucleus to protect telomeric tail end while reducing the risk of carcinogenesis through the double-mutated adenovirus-inactive telomerase and artificial mRNA-inactive telomerase. Relative to the prior art, it has the ability to prevent telomere shortening, prevent and treat a plurality of diseases associated with telomere shortening and aging; inhibit cell death caused by telomere shortening; and lengthen telomeres for the plurality of diseases associated with telomere shortening and aging cells, and have a therapeutic effect on slowed down diseases.

Of course, there may be other embodiments of the present invention, and without departing from the spirit and substance of the present invention, a person skilled in the art may make various corresponding changes and variations according to the present invention, but these corresponding changes and variations shall fall within the scope of protection of the claims of the present application.

The invention claimed is:

1. An inactive telomerase, characterized in that said inactive telomerase is a double mutant human telomerase of which the two mutation sites are Y707F and D868A, respectively.

2. An adeno-associated virus (AAV) vector, characterized in that the AAV vector expresses the inactive telomerase according to claim 1.

3. An artificial mRNA vector expressing the inactive telomerase according to claim 1.

4. A method of treating a disease associated with telomere shortening in non-dividing cells by administering the AAV vector according to claim 2 to a subject.

5. The method according to claim 4, characterized in that said non-dividing cells are selected from a cardiomyocyte, a skeletal muscle cell, or a nerve cell.

6. The method according to claim 4, characterized in that said disease associated with telomere shortening in non-dividing cells comprises diseases associated with telomere shortening in a cardiomyocyte.

7. The method according to claim 6, characterized in that said disease associated with telomere shortening in a cardiomyocyte is selected from a dilated cardiomyopathy (DCM), a hypertrophic cardiomyopathy (HCM), a nuclear fibrillar protein disease, or a telomere shortening-related rare heart disease.

8. The method according to claim 7, characterized in that said telomere shortening-related rare heart disease comprises Duchenne muscular dystrophy (DMD).

9. A method of treating-a disease associated with telomere shortening in non-dividing cells by administering the artificial mRNA vector according to claim 3 to a subject.

10. The method according to claim 9, characterized in that said non-dividing cells are selected from a cardiomyocyte, a skeletal muscle cell, or a nerve cell.

11. The method according to claim 9, characterized in that said disease associated with telomere shortening in non-dividing cells comprises diseases associated with telomere shortening in a cardiomyocyte.

12. The method according to claim 11, characterized in that said disease associated with telomere shortening in a cardiomyocyte is selected a dilated cardiomyopathy (DCM), a hypertrophic cardiomyopathy (HCM), a nuclear fibrillar protein disease, or a telomere shortening-related rare heart disease.

13. The method according to claim 12, characterized in that said telomere shortening-related rare heart disease comprises Duchenne muscular dystrophy (DMD).

* * * * *